United States Patent [19]

Furukawa et al.

[11] Patent Number: 5,089,776
[45] Date of Patent: Feb. 18, 1992

[54] APPARATUS FOR DETECTING DEFECTS IN A MOVING STEEL STRIP WITH A MAGNETIZING YOKE AND A SENSOR PLACED ON OPPOSITE SIDES OF THE STRIP

[75] Inventors: Takato Furukawa; Kenichi Iwanaga; Atsuhisa Takegoshi, all of Kawasaki, Japan

[73] Assignee: NKK Corporation, Tokyo, Japan

[21] Appl. No.: 580,138

[22] Filed: Sep. 10, 1990

[30] Foreign Application Priority Data

Sep. 25, 1989 [JP] Japan ............................. 1-111755[U]

[51] Int. Cl.$^5$ ...................... G01N 27/83; G01R 33/12
[52] U.S. Cl. ............................ 324/227; 73/159; 324/242; 324/261; 324/262; 340/675
[58] Field of Search ........ 324/206, 226, 227, 229–231, 324/235, 239–243, 261, 262; 73/159; 340/675, 676; 72/10, 11, 16

[56] References Cited

U.S. PATENT DOCUMENTS

| | | |
|---|---|---|
| 3,662,576 | 5/1972 | Girlatschek .................... 324/229 X |
| 3,781,662 | 12/1973 | Davis . | 
| 3,886,445 | 5/1975 | Chiba et al. . |
| 4,107,606 | 8/1978 | Typpo et al. ..................... 324/229 |
| 4,518,919 | 5/1985 | Ishida .............................. 324/235 X |
| 4,519,249 | 5/1985 | Hunt ................................. 73/159 X |
| 4,767,987 | 8/1988 | Montgomery ..................... 324/231 |

FOREIGN PATENT DOCUMENTS

| | | |
|---|---|---|
| 2620070 | 5/1976 | Fed. Rep. of Germany . |
| 63-107849 | 7/1988 | Japan . |
| 1311907 | 6/1970 | United Kingdom . |

Primary Examiner—Gerard R. Strecker
Attorney, Agent, or Firm—Frishauf, Holtz, Goodman & Woodward

[57] ABSTRACT

A magnetic defect detector having a pair of rotatable cylinders made of nonmagnetic material which pinch a running steel strip therebetween, two pairs of bearings being engaged with the end parts of the pair of cylinders. A pair of stationary shafts are respectively housed in the cylinders, the end parts of which are engaged with the bearings. A yoke is housed in one of the cylinders, the free ends of which are placed near to the pinched strip, and a magnetizing coil surrounds the yoke. At least one sensor is housed in the other of the cylinders, and it is placed near to the pinched strip.

22 Claims, 5 Drawing Sheets

APPARATUS FOR DETECTING DEFECTS IN A MOVING STEEL STRIP WITH A MAGNETIZING YOKE AND A SENSOR PLACED ON OPPOSITE SIDES OF THE STRIP

BACKGROUND OF THE INVENTION

1. Field of the Invention

The invention relates to the field of measuring technology. The invention relates to the field of detecting defects of steel strip by utilizing a magnetic defect detector. The apparatus of the invention is especially useful for inspection of a steel strip coated with tin and formed into a can for storing foods by a deep drawing process.

2. Description of the Related Art

In the process of making steel strip, especially tin plate strip, it is required to detect the defects on or in the strip. A recent technology in making cans for storing food is the process wherein the tin plate is deep drawn to form a part of the can corresponding to the body and the bottom end of a three piece can, into one piece, in one step. This is a great advance in can making technology. However the technology puts a heavy burden on the quality of the tin plate used for can making. In deep drawing, the severe working may cause breakage of the tin plate on the inner, or on the outer surface of the steel plate. Therefore, minor defects which may stand in the other working can be the ones of which detection is required for the tin plate utilized in the deep drawing. This improvement of the measuring technology is also beneficial to the steel plate used for general purposes.

There are related arts in this field of technology wherein detection is performed of the defects of the steel strip such as inner defects or bubbles, or surface defects, when the steel plate is stationary or running. Japanese Utility Model laid open 107849/88 dicloses such an apparatus for the detection of the defects.

Figure 3A:
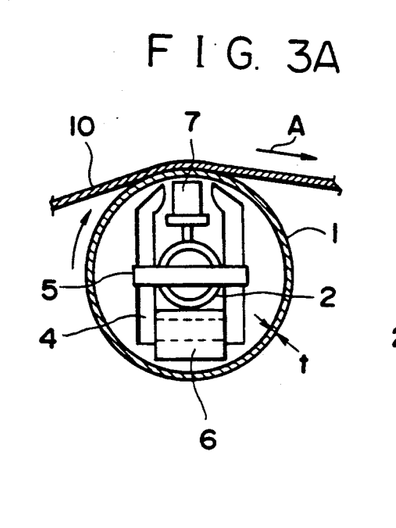
FIGS. 3A and 3B are patially cutaway sectional views of a related art.
Figure 3B:
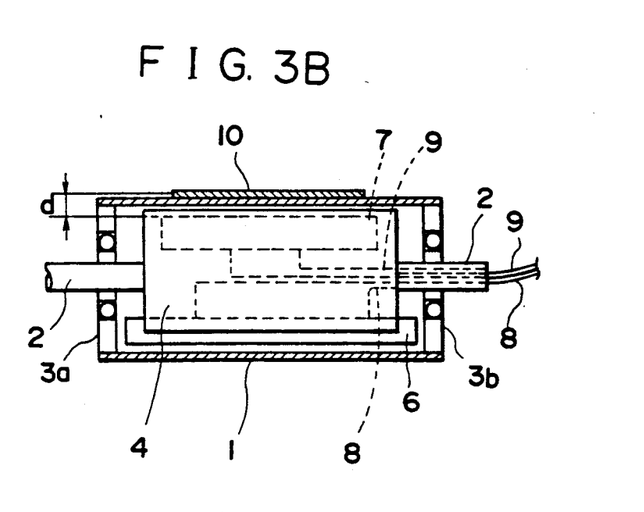

FIGS. 3A and 3B are partially cutaway sectional views of a related art, with FIG. 3A being a side view and FIG. 3B being a front view of the related art. FIGS. 3A and 3B show an apparatus which continuously detects defects of a running steel strip. In these figures, 1 denotes a hollow cylinder made of a nonmagnetic material. The shaft 2 is placed at the center of the hollow cylinder 1. The shaft 2 is fixed to a stationary body, not shown. A pair of bearings 3a and 3b are attached between the shaft and the hollow cylinder at both ends of the hollow cylinder. Accordingly, the hollow cylinder can be freely rotated around the shaft. Inside of the hollow cylinder, the magnetizing yoke 4 is fixed to the shaft by the engagement of the supporting member 5, the free ends of the yoke being placed in the vicinity of the inner surface of the cylinder. The yoke is equipped with magnetizing coil 6. Between both free ends of the yoke the magnetic detection elements 7 is placed and fixed to the shaft. The cable 8 which supplies the magnetizing electric current, and the cable 9 which takes out the signal from the magnetic detection elements are led to the outside of the hollow cylinder via the shaft. Accordingly, the magnetizing yoke and the magnetic detection elements are fixed and the hollow cylinder rotates around the yoke and the element, with little clearance between the inner surface of the cylinder and the yoke or the elements. In this configuration of the cylinder, when the strip 10 is running in the direction denoted as A, it is pressed to the cylinder by a certain force, and the cylinder rotates in that direction. When magnetizing electric current is supplied, a closed magnetic circuit is formed between the yoke and the running steel strip 10. When a defect is in existence in or on the strip, the magnetic circuit is disturbed, and a magnetic flux leakage is generated which is detected by the magnetic detection elements as a defect signal.

The detected defect signal corresponds to the magnitude of the defect at the inside or on the surface of the strip, and the the magnitude of the defect can be classified by the level of the signal.

The level of the defect signal varies with the magnetic circuit condition which is determined by the magnetizer composed of the yoke and the magnetizing coil, and the strip, and with "lift off", or the distance between the magnetic detection element and the strip, denoted as "d".

Figure 4:
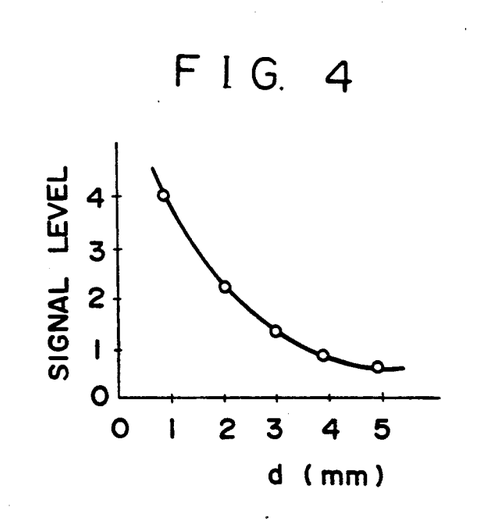
FIG. 4 is a graph showing the relationship between the distance from the free ends of the yoke to the strip and the signal level of the defect signal.

FIG. 4 is a graph showing the relationship between "d" and the signal level of the defect signal. The abscissa denotes "d" and the ordinate denotes the signal level. As shown in FIG. 4, the larger the distance between the magnetic detection elements and the strip, the smaller the signal level. To evade the problem, the "d" is maintained constant by using hollow cylinder having the thickness of "t" as shown in FIGS. 3A and 3B. The hollow cylinder is made of a nonmagnetic material since if it has magnetism, the formation of the magnetic circuit is not possible.

The magnetic circuit is stabilized when the magnetic gap between the free ends of the yoke and the strip gets smaller or the "t" gets smaller. When the "t" gets smaller, the "d" gets smaller, the signal level gets larger, and signal noise level ratio gets larger which leads to the enhancement of the accuracy of the detection. Accordingly it is desirable to make the thickness of the hollow cylinder as thin as possible.

To carry out the detection when the strip is running, the hollow cylinder and the strip should be constantly contacted. As the result of the application of the tension on the strip to make the contact with the cylinder, the downward force due to the tension and the weight of the strip is applied on the hollow cylinder which deforms the cylinder or may break it. When the cylinder is deformed, the distance between the magnetic detection element and the strip "d" can not be maintained constant. Therefore the thickness of the hollow cylinder "t" can not be made thinner than a predetermined restriction to maintain the circular shape of the hollow cylinder as long as possible.

Accordingly the apparatus of the related art shown in FIGS. 3A and 3B is incapable of performing the detection of minor defects, of the strip running in the production line or in the processing line because the thickness of the cylinder can not be as this as the desired quality requirement of the strip.

SUMMARY OF THE INVENTION

It is an object of the present invention to provide an apparatus which detects defects in a running steel strip.

It is also an object of this invention to provide a magnetic defect detector for steel strip.

The present invention provides a magnetic defect detector comprising:

a pair of rotatable cylinders made of nonmagnetic material which pinch a running steel strip;

two pairs of bearings being engaged with the end parts of said pair of cylinders;

a pair of stationary shafts housed in the pair of cylinders, the end parts of said pair of stationary shafts being engaged with said two pairs of bearings;

a yoke which generates a magnetic circuit in said strip housed in one of the pair of cylinders, the free ends of said yoke being placed in the vicinity of the inner surface of a part of the cylinder which contacts with the strip;

a magnetizing coil surrounding a part of the yoke;

a supporting element which supports the yoke and fixed to the one of said pair of shafts;

a series of sensors for detecting signals of defects of the strip caused by a magnetic leakage flux due to said defects, housed in the other one of said pair of cylinders and arranged parallel to the axis of the cylinder in the vicinity of the inner surface of a part of the cylinder which contacts with the strip; and a second supporting element which supports said series of sensors and fixed to the other one of said pair of shafts.

The thickness of the cylinder which houses the magnetic defect detector can be further decreased when the thickness of the part of the cylinder under the magnetic detecting elements is made thinner than the parts of the cylinder between the magnetic detecting elements without affecting the structural strength of the cylinder.

This invention can be utilized with a surface defect detector which detects a surface defect of the strip. When the surface defect detector detects a surface defect at a certain spot of the strip and the magnetic defect detector of this invention does the detection, the defect is defined as a surface defect of the strip. When the surface defect detector does not detect a surface defect at a certain spot of the strip and the magnetic defect detector of this invention generates a defect signal, the defect is defined as an inner defect of the strip.

This invention can be utilized with a weld detector which detects the welded part of the strip. When the weld detector detects the welded part of the strip and the magnetic defect detector of this invention detects the welded part, the weld is not classified as a defect of the strip.

The material of the cylinder should be nonmagnetic, but it should not be the one which can generate an eddy current in the rotation of the cylinder which may disturb the accuracy of the detection of the magnetic detecting elements. Therefore the material should have high electric resistance. In this embodiment, an austenitic steel is utilized. However titanium, synthetic resin, fiber reinforced plastic, and ceramics are good substitutes.

BRIEF DESCRIPTION OF THE DRAWINGS

FIG. 7 depicts a block diagram of control circuit 18 of FIG. 2.

BRIEF DESCRIPTION OF THE PREFERRED EMBODIMENTS

The problem encountered in the related art is that the distance between the sensor and the strip cannot be minimized to assure the accuracy of the sensor due to the fact that the thickness of the hollow cylinder cannot be made as thin as required. The problem lies in the structure of the sensing system. The present invention has solved the problem by adopting two cylinder system; one encloses the magnetizing unit and the other encloses the sensor. The both cylinders pinch the strip and the applied tension on the strip and the weight of the strip act on the cylinder which encloses the magnetizer. No significant force is designed to be applied on the cylinder which encloses the sensor unit. The thickness of the cylinder which encloses the magnetizer unit can be increased by increasing the magnetizing power. The thickness of the cylinder which encloses the sensor unit can be as thin as possible so that the desired accuracy can be attained by minimizing the distance between the sensor and the strip.

The thickness of the cylinder which houses the magnetic defect detector can be further decreased when the thickness of the cylinder under the magnetic detecting elements is made thinner than the part of the cylinder between the magnetic detecting elements without affecting the structural strength of the cylinder.

This invention can be utilized with a surface defect detector which detects the surface defect of the strip. When the surface defect detector detects a surface defect at a certain spot of the strip and the magnetic defect detector of this invention does the detection at the spot, the defect is defined as a surface defect of the strip. When the surface defect detector does not detect a surface defect at a certain spot of the strip and the magnetic defect detector of this invention generates a defect signal at the spot, the defect is defined as an inner defect of the strip. This invention can be utilized with a weld detector which detects the welded part of the strip. When the weld detector detects the welded part of the strip and the magnetic defect detector of this invention also detects the welded part, the weld is not classified as a defect of the strip.

The material of the cylinder should be nonmagnetic, and it should not be one which can generate an eddy current as the cylinder rotates since this may disturb the accuracy of the detection of the magnetic detecting elements. Therefore the material should have high electric resistance. In this embodiment, an austenitic steel is utilized. However titanium, synthetic resin, fiber reinforced plastic, and ceramics are good substitutes.

It is required for the hollow cylinder which houses the magnetizing unit to have an angle of contact for the strip in applying the tension on the hollow cylinder. Moreover this angle of contact is favorable for the magnetizer to magnetize the strip enough for the detection of the defect of the strip.

The arrangement of the two hollow cylinders in the strip production lines or in the strip processing lines wherein high line tension is applied on the strip, is quite simple since high tension is applied on the strip and a sufficient angle of contact can be procured by slightly deviating the position of the part of the contact off the otherwise straight line of the strip.

However when the line tension is low, two pinch rolls are required at the front and back sides of the hollow cylinders.

FIGS. 5A, 5B, 5C, and 5D are the schematic illustration showing the arrangement of the hollow cylinders and the pinch rolls.

Figure 5A:
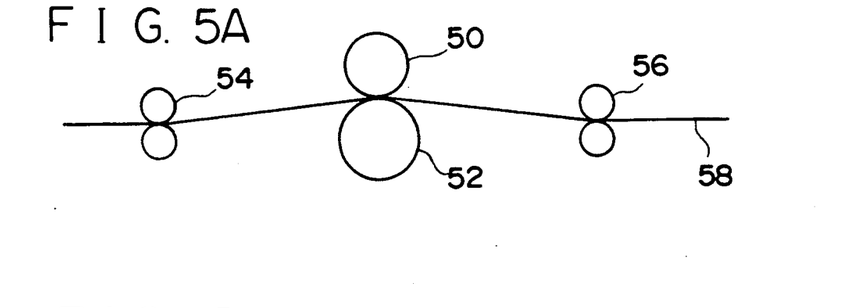
FIGS. 5A, 5B, 5C, and 5D are the schematic illustration showing the arrangement of the hollow cylinders and the pinch rolls.

FIG. 5A shows the most standard type of the arrangement. As shown in FIG. 5A, the hollow cylinder 50 which houses the sensor is placed on top of the hollow cylinder 52 which houses the magnetizer. The strip 58 is bent by the front pinch roll 54, hollow cylinder 52, and the back pinch roll 56. The plane which passes both center lines of the hollow cylinders is vertical. In this case the burden of the tension of the strip 58 and the weight thereof is supported by the hollow cylinder 52, front pinch roll 54, and back pinch roll 56.

Figure 5B:
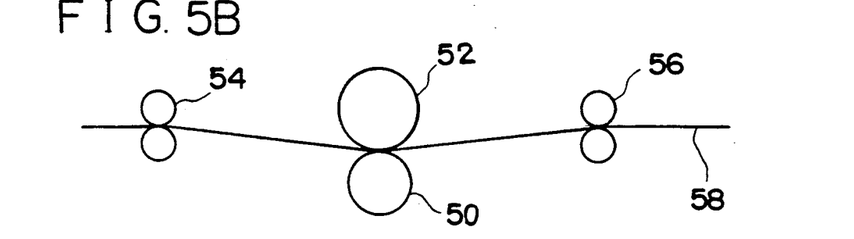

In FIG. 5B, the hollow cylinder 52 is placed on top of the hollow cylinder 50. The recipients of the burden are the same as in the case of FIG. 5A.

Figure 5C:
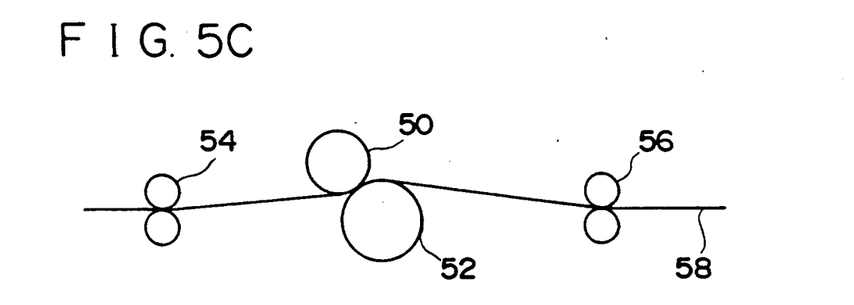
Figure 5D:
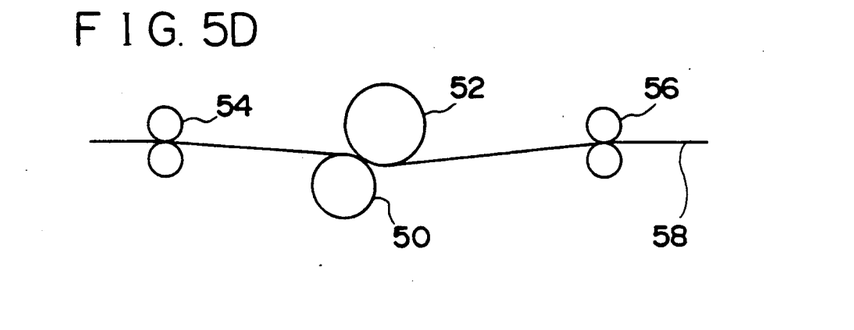

In FIGS. 5C and 5D, the plane which passes both center lines of the hollow cylinders is slanted with respect to a vertical plane. In these cases an angle of contact is procured also for the hollow cylinder 50 which ensures the contact thereof by a small contact force compared with the cases in FIGS. 5A and 5B in order to rotate the cylinder by running of the strip. In case of FIG. 5C, the hollow cylinder 50 is placed on top of the hollow cylinder 52. In case of FIG. 5D, the hollow cylinder 52 is placed on top of the hollow cylinder 50.

EXAMPLES

Figure 1A:
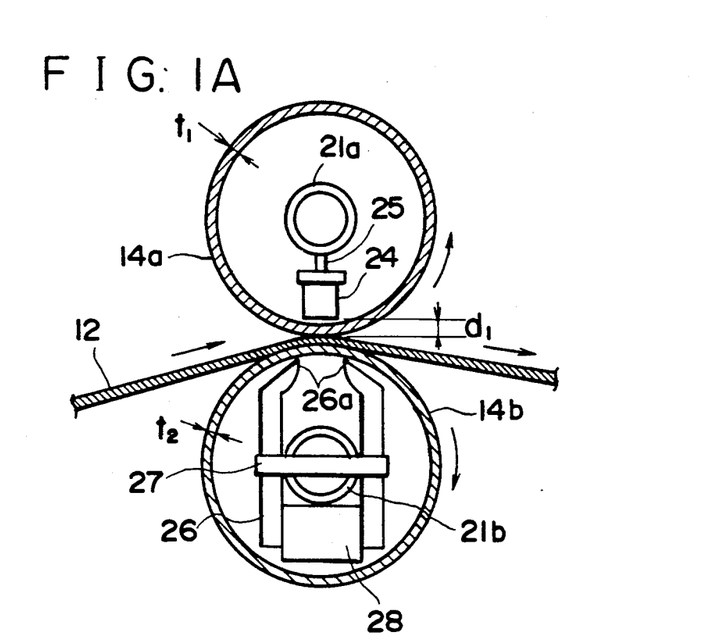
FIG. 1A is a partially cutaway side view of an embodiment of the invention.
Figure 1B:
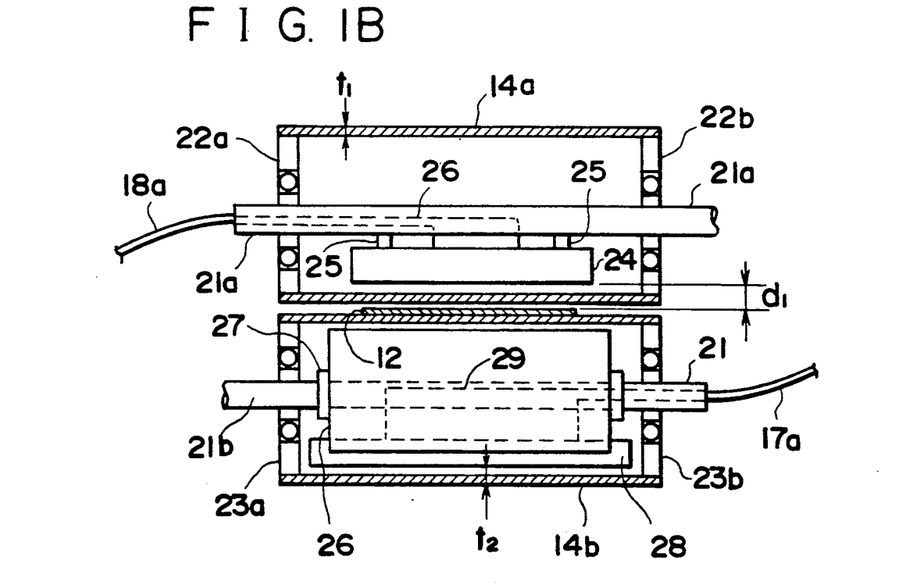
FIG. 1B is a partially cutaway front view of an embodiment of the invention.
Figure 2:
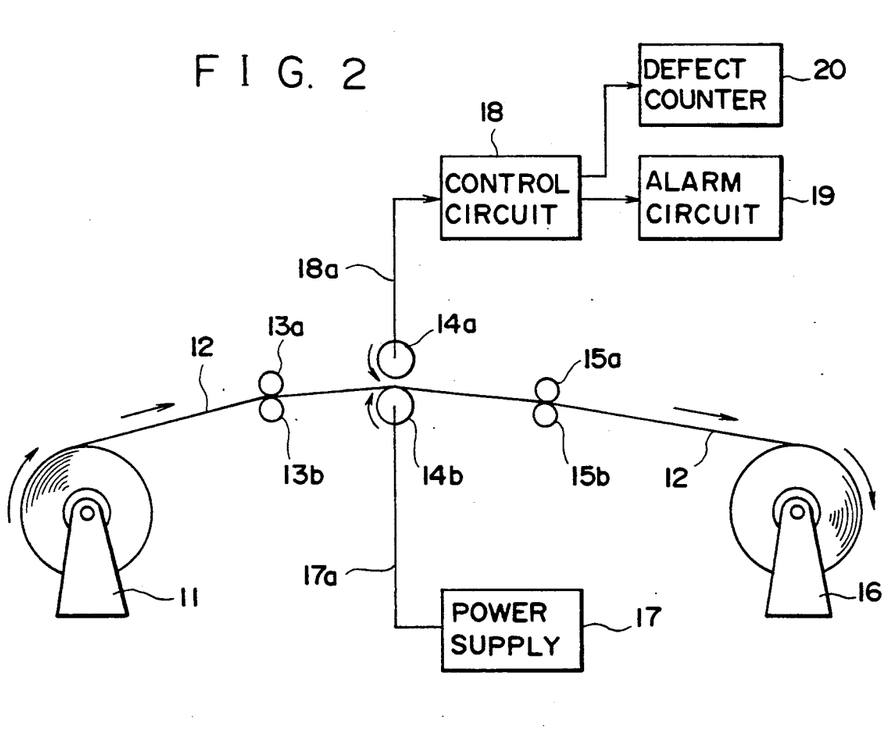
FIG. 2 is an explanatory view showing the system flow of an embodiment of the invention.

FIG. 2 is an explanatory view showing the system flow of an embodiment of the invention. The strip 12 running out of the pay off reel 11 is introduced between a pair of the cylinders 14a and 14b via the forward pinch rolls 13a and 13b, travels through the backward pinch rolls 15a and 15b, and coiled by the tension reel 16. The power supply for magnetization 17 is connected to the inside of the cylinder 14b by the cable 17a. The control circuit 18 is connected to the inside of the cylinder 14a by the cable 18a. The control circuit is connected to the defect counter 20 and the alarm circuit 19. FIG. 1A is a partially cutaway side view of an embodiment of the invention. The section of the embodiment is cut by a plane parallel to the travelling direction of the strip. FIG. 1B is a partially cutaway front view of the embodiment of the invention. The section of the embodiment of the invention is cut by a plane perpendicular to the travelling direction of the strip.

The hollow cylinders 14a and 14b protect the instrumentations from directly contacting the strip. Those cylinders are made of nonmagnetic materials to enable the magnetic flux to penetrate from inside of the cylinders to the strip. The hollow stationary shafts 21a and 21b are placed at the center of the hollow cylinders 14a and 14b. A pair of bearings 22a and 22b are inserted between the end parts of the shaft 21a and the hollow cylinder 14a. A pair of bearings 23a and 23b are inserted between the end parts of the shaft 21b and the hollow cylinder 14b. The shaft 21b is fixed to a stationary body, not shown. The shaft 21a is engaged with the shaft 21b by a weak spring, not shown. As explained above, a cylinder should be constantly in contact with the moving strip. The spring is provided to maintain such constant contact. Accordingly the hollow cylinders 14a and 14b can freely be rotated around the shafts 21a and 21b.

Inside of the hollow cylinder 14a, the magnetic detection elements 24 are arrayed parallel to the axial direction of the hollow cylinder 14a and the array is placed in the vicinity of the part of the hollow cylinder which contacts to the strip 12. The magnetic detection elements are fixed to the shafts 21a by the engagement of the supporting element 25. The clearance between the tip of the magnetic detection elements 24 and the inner surface of the hollow cylinder 14a is very small.

The defect signal generated by the magnetic detection elements is sent to the control circuit 18 via the cable 18a. Inside of the hollow cylinder 14b, the magnetic yoke 26 is fixed to the shaft 21b by the engagement of the supporting element 27. Supporting elements 27 are fixed to shaft 21b, and yoke 26 is secured therebetween. The free ends 26a of the magnetic yoke 26 is placed in the vicinity of the part of the hollow cylinder 14b which contacts to the strip. The magnetic yoke is magnetized by the magnetizing coil 28 attached to the yoke. The magnetizing electric current for the magnetic coil is supplied by the power supply 17 by the cable 17a led into the hollow shaft 21b.

The magnetic detection elements 24 are placed at the opposite side of the free ends of the yoke 26a with respect to the contact point of the strip 12 and the hollow cylinders 14a and 14b.

The distances between the magnetic detection elements and the strip 12, denoted as "$d_1$", and between the free ends of the yoke 26a, are fixed.

When the strip runs in the direction denoted in FIG. 2, the hollow cylinder 14b is rotated in the direction denoted in FIG. 2 as it is driven by the frictional force generated through the contact force produced by the tension of the strip and the weight thereof. The hollow cylinder 14a is also rotated since the cylinder is pressed to the strip by a spring mechanism, not shown.

When the power supply 17 supplies electric current to the magnetic coil, a closed magnetic circuit is formed between the magnetic yoke 26 and the strip 12 since the hollow cylinders are made of nonmagnetic material. When a defect inside of or on the surface of the strip passes through the magnetic circuit, the magnetic circuit is disturbed and a magnetic flux leakage is generated which is detected by the magnetic detection elements 24 as a defect signal.

The defect signal outputted by the magnetic detection elements is inputted to the control circuit 18. The control circuit specifies a measured signal as a defect when the level is higher than a predetermined value. The specified defect signal is sent to the alarm circuit 19 which generates an alarm to operators. The specified defect signal is also sent to the defect counter 20 which updates the counted number of defects.

Details of control circuit 18 are shown in FIG. 7. Defect detection circuit 18a receives the magnetic defect signal from the sensor 24 and compares it against the reference signal. If the latter is exceeded, circuit 18a determines that a defect exists in the strip. Surface detection circuit 18b compares the defect signal outputted by circuit 18a with a surface defect signal obtained from a surface defect detector (not shown). When a defect is detected by circuit 18a and the surface defect signal also indicates the presence of a surface defect, the defect is identified as a surface defect. An alarm is triggered when one or both of the defect signal and the surface defect signal are generated. Similarly, weld detection circuit 18c compares the output of circuit 18a with a weld signal from a weld detector (not shown). When both the existence of a defect is indicated by circuit 18a and the weld signal indicates the presence of weld, the defect is identified as a weld. An alarm is triggered when one or both of the defect signal and the weld signal are generated.

In FIG. 1B, 46 denotes a wiring cord for elements 24, and 29 denotes a wiring cord for magnetizing coil 28. The magnetic detection element wiring cord 46 and the magnetic wiring cord 29 each pass through the hollow shafts 21a and 21b leading through holes made at appropriate locations of the shafts, respectively, to the magnetic detection elements 24 and the magnetizing coil 28.

The thickness of the hollow cylinders which house the instrumentation is determined by the deformation of the cylinder and the capabilities of the instrumentation.

As for the thickness of the hollow cylinder 14b denoted as $t_2$ in FIG. 1A, consideration should be given to the deformation of the cylinder 14b due to the tension applied on it and the weight of the strip which is also applied on the hollow cylinder 14b. There should be enough thickness to prevent the deformation so that the free ends of the yoke 26a do not touch the inner surface of the hollow cylinder. To generate enough magnetic flux to detect the defect of the strip, the free ends of the yoke should approach the strip as near as possible. However this problem can be solved by providing a strong magnetizing capacity. As for the thickness of hollow cylinder 14a denoted as $t_1$ in FIG. 1A, no significant external force is applied on the hollow cylinder 14a. However some external force should be applied on the hollow cylinder 14a and the hollow cylinder should be pressed to the strip in order for the hollow cylinder to be driven by the strip. In spite of the above-mentioned facts the thickness of the hollow cylinder can be decreased to the extent wherein the magnetic detecting elements are enabled to detect the defect of the strip since no significant external forces are applied on the hollow cylinder. The smaller the value $t_1$, the more improved the S/N ratio of the defect signal, which enhances the accuracy of the detection.

In this embodiment, $t_1$ is desirable to be in the range of at least 1 mm to provide adequate structural strength for the cylinder, and at most 5 mm to provide a sufficient sensing capability.

The thickness of the cylinder $t_1$ can be further decreased when the thickness of the cylinder under the magnetic detecting elements is made thinner than the part of the cylinder between the magnetic detecting elements; in other words a stepped inner surface of the hollow cylinder is provided.

Figure 6:
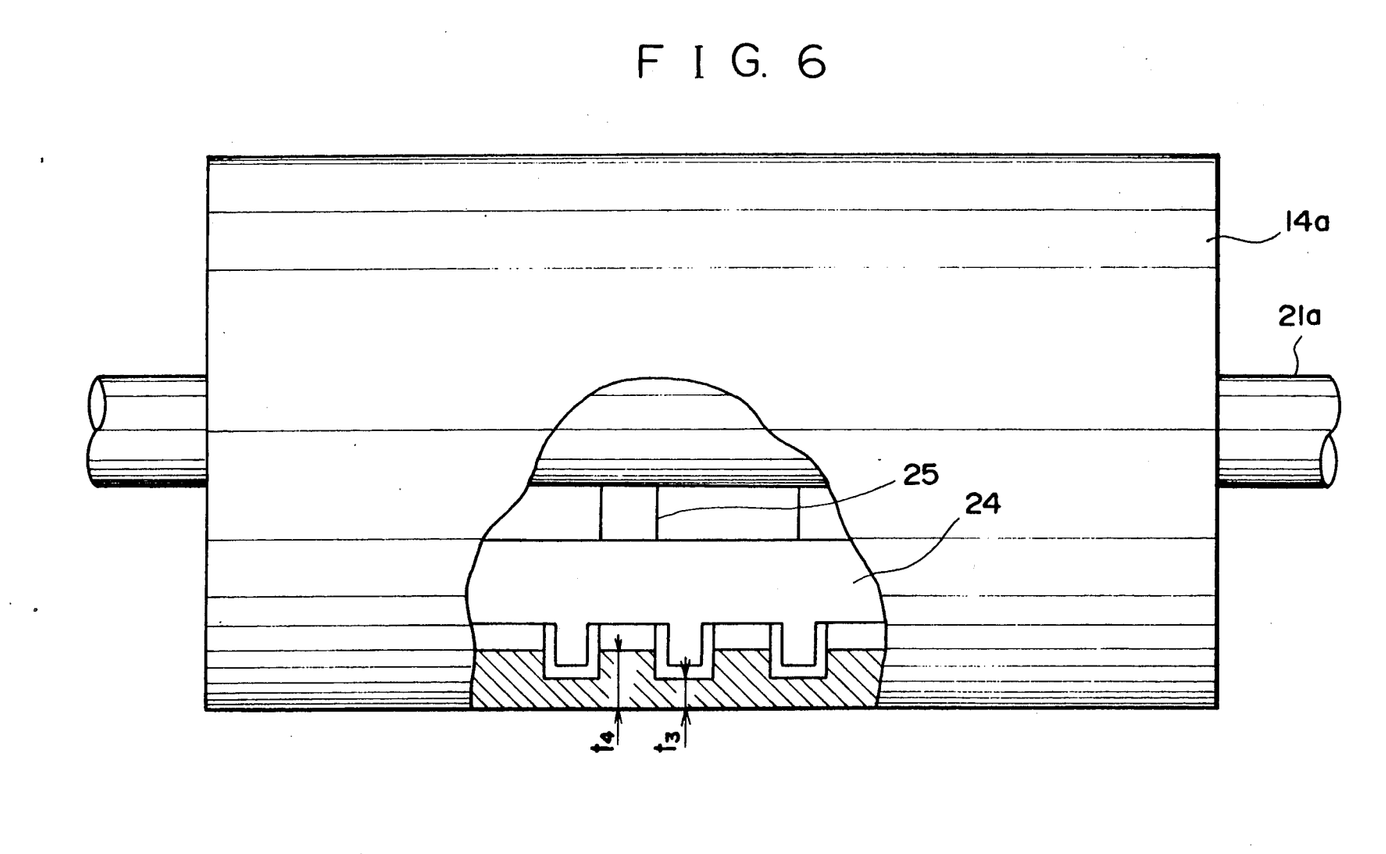
FIG. 6 is a partially cutaway view of an embodiment of the invention.

FIG. 6 is a partially cutaway view of an embodiment of the invention. The thickness of the hollow cylinder 14a under the magnetic detecting elements 24, denoted as $t_3$, is thinner than the thickness of the cylinder 14a between the magnetic detecting elements 24, denoted as $t_4$.

In this embodiment, an austenitic steel is utilized. However titanium, synthetic resin, fiber reinforced plastic, and ceramics are good substitutes.

In this embodiment, the material of the magnetizing coil is a pure iron which has high performance in magnetizing of the yoke.

What is claimed is:

1. A magnetic defect detector comprising:

a pair of rotatable cylinders made of nonmagnetic material which pinch a running steel strip therebetween;

two pairs of bearings in said pair of cylinders, respectively;

a pair of stationary shafts respectively housed in the pair of said cylinders, respective portions of one of said pair of stationary shafts being engaged with one of said two pairs of bearings, and respective portions of the other of said pair of stationary shafts being engaged with the other of said two pairs of bearings;

a yoke which generates a magnetic circuit in said strip housed in one of the pair of cylinders, free ends of said yoke being in the vicinity of an inner surface of a part of said one cylinder which contacts the strip;

a magnetizing coil surrounding a part of the yoke;

a supporting element fixing the yoke to one of the pair of shafts housed in said one cylinder so as to also be housed within said one cylinder;

at least one sensor having means for detecting signals indicative of defects of the strip caused by a magnetic leakage flux due to said defects, said at least one sensor being housed in the other one of said pair of cylinders and arranged in the vicinity of an inner surface of a part of said other cylinder which contacts the strip; and a second supporting element fixing said at least one sensor to the other one of the pair of stationary shafts such as to also be housed within said other cylinder.

2. The magnetic defect detector of claim 1, wherein the thickness of parts of the cylinder under the at least one sensor is smaller than the thickness of parts of the cylinder situated laterally of the at least one sensor.

3. The magnetic defect detector of claim 2, wherein the thickness of parts of the cylinder under the sensor is not less than 1 mm and not more than 5 mm.

4. The magnetic defect detector of claim 1, further comprising:

a signal treating circuit wherein a signal from the magnetic defect detector is compared with a second signal from a surface defect detector; and a signal specifying circuit which specifies the signal from the magnetic defect detector as the surface defect of the strip when the both signals are generated at the same spot of the strip and as the inner defect of the strip when the signal from the surface defect detector is not generated at the spot and the signal from the magnetic defect detector is generated.

5. The magnetic defect detector of claim 1, further comprising:

a signal treating circuit wherein a signal from the magnetic defect detector is compared with a second signal from a weld detector; and a signal specifying circuit which specifies the signal from the magnetic defect detector is a welded part of the strip when the signal from weld detector is generated.

6. The magnetic defect detector of claim 1, wherein the material of the cylinders is an austenitic stainless steel.

7. The magnetic defect detector of claim 1, wherein the material of the cylinders is a titanium alloy.

8. The magnetic defect detector of claim 1, wherein the material of the cylinders is a synthetic resin.

9. The magnetic defect detector of claim 1, wherein the material of the cylinders is a fiber reinforced plastic.

10. The magnetic defect detector of claim 1, wherein the material of the cylinders is a ceramics.

11. The magnetic defect detector of claim 2, wherein the material of the cylinders is an austenitic stainless steel.

12. The magnetic defect detector of claim 2, wherein the material of the cylinders is a titanium alloy.

13. The magnetic defect detector of claim 2, wherein the material of the cylinders is a synthetic resin.

14. The magnetic defect detector of claim 2, wherein the material of the cylinders is a fiber reinforced plastic.

15. The magnetic defect detector of claim 2, wherein the material of the cylinders is a ceramics.

16. The magnetic defect detector of claim 1, wherein the material of the magnetic coil is a pure iron.

17. The magnetic defect detector of claim 2, wherein the material of the magnetic coil is a pure iron.

18. The magnetic defect detector of claim 1, further comprising:
   a first pair of pinch rolls in contact with said strip and placed at a side of the hollow, rotatable cylinders at which said steel strip enters; and
   a second pair of pinch rolls in contact with said strip and placed at a side of the hollow, rotatable cylinders at which said steel strip exits, wherein the part of the cylinders in contact with the strip is spaced from a horizontal plane which includes parts of said first and second pairs of pinch rolls in contact with the strip.

19. The magnetic defect detector of claim 18, wherein the other cylinder which houses the at least one sensor is placed on top of the one cylinder which houses the yoke, wherein a plane which includes the center lines of the cylinders is vertical.

20. The magnetic defect detector of claim 18, wherein the one cylinder which houses the yoke is placed on top of the other cylinder which houses the at least one sensor, wherein a plane which includes the center lines of the cylinders is vertical.

21. The magnetic defect detector of claim 19, wherein the other cylinder which houses the at least one sensor is placed on top of the one cylinder which houses the yoke, wherein a plane which includes the center lines of the cylinders is slanted with respect to a vertical plane.

22. The magnetic defect detector of claim 20, wherein the one cylinder which houses the yoke is placed on top of the other cylinder which houses the at least one sensor, wherein a plane which includes the center lines of the cylinders is slanted with respect to a vertical plane.

* * * * *